United States Patent [19]

Curtze et al.

[11] Patent Number: 5,656,630

[45] Date of Patent: Aug. 12, 1997

[54] METHOD OF COMBATING FUNGUS

[75] Inventors: Jürgen Curtze, Geisenheim-Johannisberg; Guido Albert, Hackenheim; Dietrich Eichler, Gau-Algesheim, all of Germany

[73] Assignee: American Cyanamid Company, Parsippany, N.J.

[21] Appl. No.: 339,385

[22] Filed: Nov. 14, 1994

[30] Foreign Application Priority Data

Nov. 15, 1993 [DE] Germany .................. 93 11 8442.8

[51] Int. Cl.$^6$ ................................. A61K 31/535
[52] U.S. Cl. ................................. 514/237.5
[58] Field of Search ................................. 514/237.5

[56] References Cited

PUBLICATIONS

Worthing et al, The Pesticide Manual, 9th Ed. (1991) p. 296.
Albert, G., et al., *Dimethomorph (CME 151), A Novel Curative Fungicide*, Brighton Crop Protection Conference–Pests and Diseases 1988. pp. 17–24.

*Primary Examiner*—Allen J. Robinson
*Attorney, Agent, or Firm*—Gregory M. Hill

[57] ABSTRACT

The invention relates to a method of combating fungus which comprises treating plants subject to or subjected to fungal attack, seeds of such plants or the medium in which such plants are growing or are to be grown with the Z-isomer of 4-[3-(4-chlorophenyl)-3-(3,4-dimethoxyphenyl)acryloyl] morpholine or with a composition comprising a carrier and, as active ingredient, the said Z-isomer; and the use of the Z-isomer as a fungicide.

3 Claims, No Drawings

METHOD OF COMBATING FUNGUS

This invention relates to a method of combating fungus using the Z-isomer of dimethomorph and the use of said Z-isomer as a fungicide.

Dimethomorph is the common name for a mixture of the E- and Z-isomers of 4-[3-(4-chlorophenyl)-3-(3,4-dimethoxyphenyl)-acryloyl]morpholine. This compound, which is covered by EP 0120321, is a fungicide which is effective in the control of plant diseases caused by Oomycetes, particularly those caused by members of the family Peronosporaceae and the genus Phytophthora but not Pythium, in vines, potatoes and tomatoes.

In Brighton Crop Protection Conference, 1988, 17–24 it is reported that in vitro tests on *Phytophthora infestans* have shown that, if sunlight is excluded, only the Z-isomer of dimethomorph is fungitoxic. However, in the presence of light, isomerisation takes place with a fast equilibration to a Z:E ratio of about 80:20 and therefore, under field conditions, different ratios of E- and Z-isomers have been shown to be equally effective.

It has now been discovered in tests on tomato plants that the Z-isomer of dimethomorph is much better absorbed by the roots and translocated into the leaves than the E-isomer resulting in about 5 times higher initial concentrations of the Z-isomer in the leaves than the E-isomer. This is particularly surprising since the E-isomer has a much higher water solubility (30 mg/l) than the Z-isomer (7 mg/l) and a more favourable log p value (which indicates the distribution of a compound in a water/octanol system) regarding systemic uptake of a fungicide of 2.63 at 20° C. compared to 2.73 for the Z-isomer. Moreover, the tests also showed that the concentration of Z-isomer in the leaves is much higher than the concentration of Z-isomer in the solution applied to the plant thereby indicting an accumulation of the Z-isomer in the green plant. Consequently, if pure Z-isomer is applied in conditions which substantially exclude sunlight, lower amounts of Z-isomer are required than of the E/Z mixture to achieve the same fungicidal effect and the effect is achieved quicker. This is clearly advantageous from both an economic and ecological point of view.

According to the present invention there is therefore provided a method of combating fungus which comprises treating plants subject to or subjected to fungal attack, seeds of such plants or the medium in which such plants are growing or are to be grown with the Z-isomer of 4-[3-(4-chlorophenyl)-3-(3,4-dimethoxyphenyl)acryloyl]morpholine or with a composition comprising a carrier and, as active ingredient, the said Z-isomer substantially in the absence of sunlight.

In this specification, treatment substantially in the absence of sunlight embraces treatment in the complete absence of sunlight and treatment under conditions where the Z-isomer is exposed to sunlight for such a short period of time that interconversion between the E- and Z- forms cannot take place to any significant degree. For instance, plants may be sprayed at night or transferred to a dark compartment for spraying with the Z-isomer or the Z-isomer may be applied to the roots of the plants either directly, for instance, by means of hydroponic cultivation techniques, or indirectly, preferably by means of a soil drench. Alternatively, seeds of plants may be treated with the Z-isomer and then kept under dark conditions until use.

Spraying plants at night or under dark conditions is a particulary useful technique in the curative treatment of plant diseases. Generally, there is a relatively short period of time when a fungus has penetrated the leaf of a plant but the disease has not broken out when the disease may still be stopped. For instance, in the case of Phytophthora infestans, which has a 3–5 day infection cycle, if infection occurs at day 1, treatment of the plant at day 3 will stop the disease breaking out if an effective dose is applied. Thus, it is particularly advantageous to apply only the Z-isomer of dimethomorph in such circumstances since this will be more readily absorbed into the leaves than the E-isomer and can therefore act more quickly and effectively.

Dimethomorph is normally applied as a spray at dosages of 0.09 to 0.5 kg/ha to achieve effective prophylactic activity. However, in the case of a curative spray, effective treatment may be achieved by applying the Z-isomer at dosages of 0.025 to 0.25 kg/ha.

If the Z-isomer of dimethomorph is to be applied by means of a soil drench, the dosage required will depend on the crop to be treated, the medium in which the crop is growing and the conditions under which the crop is growing, that is, greenhouse or field conditions. For instance, for treatment of crops growing in a sandy soil substrate in individual pots under greenhouse conditions, a dosage of 0.01 to 5 kg/ha, preferably 0.1 to 2 kg/ha, may be used whereas under field conditions, where the volume of soil to be treated is greater, dosages of 5 to 10 kg/ha may be required. It is therefore preferred that the Z-isomer be applied at a dose rate in the range from 0.01 to 10 kg/ha.

The Z-isomer may be used to control the same diseases as E/Z dimethomorph. However, it is particularly effective in combating *Phytophthora infestans* and *Plasmopara viticola*, as well as soil-borne Phytophthora diseases and seed- and seedling-attacking downy mildews, such as *Plasmopara halstedii*.

The Z-isomer may be prepared by selective crystallisation of the Z-isomer from a solution containing a mixture of the E-isomer and Z-isomer and subsequent isomerisation of the remaining E-isomer to form a mixture of the E-isomer and Z-isomer.

This method is based on the fact that, as mentioned above, the Z-isomer has a lower solubility than the E-isomer thereby allowing the Z-isomer to be selectively crystallised and removed from the mother liquor, for instance, by filtration. Sufficient E/Z dimethomorph may then be added to the remaining mother liquor to restore it to its original concentration and the mixture is then preferably heated with a catalyst for isomerisation, particularly an acid or basic catalyst, such as toluenesulphonic acid, trifluoromethanesulphonic acid, Nafion (Trade Mark: a perfluorinated ion-exchange membrane), Amberlyst (Trade Mark: a macroreticular ion-exchange resin), sodium tert-butoxide or sodium methoxide, for several hours to restore the E/Z ratio to approximately 1:1. The Z-isomer can then be selectively crystallised as described above and the process repeated several times until nearly all of the E-isomer has been converted into the Z-isomer.

The above process is carried out in the presence of a suitable solvent. Preferably, the solvent is toluene.

The Z-isomer may be used in the method of the invention in the form of a composition which comprises a carrier and, as active ingredient, the said Z-isomer. Such a composition preferably contains from 0.5 to 95% by weight of the Z-isomer.

A carrier in such a composition is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol, benzyl alcohol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in the composition is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ½–10% w of active ingredient. Granules are usually prepared to have a size between 10 and 100 BS mesh (1.676 - 0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition may also contain other ingredients, for example other compounds possessing herbicidal, insecticidal or fungicidal properties or fertilisers.

Of particular interest in enhancing the duration of the protective activity of the Z-isomer is the use of a carrier which will provide a slow release of the Z-isomer into the environment of the plant which is to be protected. Such slow-release formulations could, for example, be inserted in the soil adjacent to the roots of a tobacco or vegetable plant, or could include an adhesive component enabling them to be applied directly to the stem of a vine plant.

The invention still further provides the use as a fungicide of the Z-isomer of 4-[3-(4-chlorophenyl)-3-(3,4-dimethoxyphenyl)acryloyl]morpholine or a composition as defined above.

The present invention is of wide applicability in the protection of crop plants against fungal attack. Typical crops which may be protected include vines, tobacco and vegetables, such as potatoes and tomatoes. The duration of protection is normally dependent on a variety of external factors, such as climate, whose impact is normally mitigated by the use of a suitable formulation.

The invention is further illustrated by the following examples.

EXAMPLE 1

Measurement of prophylactic activity against *Phytophthora infestans* on tomatoes after soil drench Method After the developemnt of the cotyledons, tomato plants (cv Prof. Rudloff) were transferred into 6 cm plastic pots containing coarse sand+10% sandy soil substrate. The plants were kept in a greenhouse at 23° C. day temperature and 18° C. night temperature. Relative humidity was between 50 and 70%. When the first leaves had developed the plants were ready for fungicide application.

6 plants per treatment were used. Application of the fungicides was carried out 2 days before infection. 5 ml of the fungicide solution were drenched to the substrate with a pipette. The plants were then kept in the greenhouse at 23° C. day and 18° C. night temperature and 50–70% relative humidity.

The plants were artificially infected with an aqueous spore suspension of Phytophthora infestans containing 300.000 spores/ml. Infection was accomplished by spraying the upper side of the leaves with the spore suspension. Then the plants were immediately incubated at 100% humidity for 48 hours in the dark. Symptoms developed rapidly when the plants were transferred into the greenhouse with low relative humidity (approximately 50%).

Evaluation was carried out by estimating the percentage of diseased leaf area of each individual leaf. The activity in % was calculated using the ABBOTT formula:

$$\% \text{ activity} = 100 - \frac{\% \text{ infection in treated}}{\% \text{ infection in untreated}} \times 100$$

Results

| Concentration of active ingredient | Activity in % | | |
|---|---|---|---|
| | E/Z 50:50 | E | Z |
| 100.00 ppm | 100 | 97 | 100 |
| 50.00 ppm | 100 | 94 | 100 |
| 25.00 ppm | 100 | 71 | 100 |
| 12.50 ppm | 98 | 47 | 100 |
| 6.25 ppm | 91 | 16 | 100 |

(NB. Under the conditions of this experiment, concentrations of 100, 50, 25, 12.5 and 6.25 ppm correspond to dosage rates of 1.76, 0.88, 0.44, 0.22 and 0.11 kg/ha respectively.)

EXAMPLE 2

Preparation of the Z-isomer of 4-[3-(4-chlorophenyl)-3-(3, 4-dimethoxyphenyl)acryloyl]morpholine 25 g 4-[3-(4-Chlorophenyl)-3-(3,4-dimethoxyphenyl) acryoyl]morpholine (E:Z 70:30) in 200 ml toluene were heated with 2.5 g para-toluenesulphonic acid for 5 hours under reflux resulting in an E:Z ratio of approximately 50:50. After removal of the para-toluenesulphonic acid and cooling. 9.5 g pure Z-isomer crystallised out. A further 10 g of 4-[3-(4-chlorophenyl)-3-(3,4-dimethoxyphenyl)acryloyl] morpholine (E:Z 70:30) and 2.5 g paratoluenesulphonic acid were then added to the mother liquor and treated as described above to give a further 9.6 g pure Z-isomer.

EXAMPLE 3

Separation of the Z-isomer of 4-[3-(4-chlorophenyl)-3-(3,4-dimethoxyphenyl)acryloyl]morpholine and isomerisation of the residual mixture to an E/Z ratio of 50/50

100 g Crude 4-[3-(4-chlorophenyl)-3-(3,4-dimethoxyphenyl)acryloyl]morpholine (96.5% pure, E/Z= 47/53) was dissolved in 800 ml toluene whilst being heated to 70° C. On cooling to room temperature, a substance crystallised out which was left to stand for at least 4 hours and then drawn off by suction. The filter cake was first washed with 100 ml toluene, then with 100 ml methanol and dried.

Yield: 33.5–38.5g * Z-isomer, containing 2% E-isomer, 98.4% M.pt. 166°–7° C.

(* signifies mean value from several experiments)

The toluene filtrate still contains about 60 g residual 4-[3-(4-chlorophenyl)-3-(3,4-dimethoxyphenyl)acryloyl] morpholine. It was mixed with 3.0 g 4-toluenesulphonic acid (5% by weight in relation to residual dimethomorph) and stirred under reflux for 8 hours. It was then cooled to 60° C., extracted 3 times with 50 ml portions of water and 750 ml was distilled off on a rotary evaporator. The concentrate was cooled to 50° C. and 250 ml petroleum ether was run in whilst the mixture was stirred vigorously. The substance then precipitated out in solid form. After leaving it to stand for 1 hour, the substance was drawn off by suction, washed with 100 ml petroluem ether and dried.

Yield: 58.8g E/Z mixture (48/52), 98.7%, M.pt. 127°–140° C.

EXAMPLE 4

Isomerisation can also be carried under basic conditions using sodium tert-butoxide according to the method of Example 3.

When 3.0 g sodium tert-butoxide is added (5% by weight in relation to residual dimethomorph) and boiling is carried out for 8 hours, the yield is 56.1 g, E/Z=44/56, 98.2%.

EXAMPLE 5

Separation of the Z-isomer and isomerisation of the residual mixture to an E/Z ratio of 70/30

100 g Crude 4-[3-(4-chlorophenyl)-3-(3,4-dimethoxyphenyl)acryloyl]morpholine (96.5% pure, E/Z= 47/53) was dissolved in 800 ml toluene whilst being heated to 70° C. On cooling to room temperature, a substance crystallised out which was left to stand for at least 4 hours and then drawn off by suction. The filter cake was first washed with 100 ml toluene, then with 100 ml methanol and dried.

Yield: 37.3 g Z-isomer, containing 2% E-isomer, 98.4%, M.pt. 166°–7° C.

The methanol filtrate was discarded and 750 ml was distilled off from the toluene filtrate on a rotary evaporator. The concentrate was cooled to 50° C. and 250 ml petroleum ether was run in under vigorous stirring whereupon the substance precipitated out in solid form. It was then cooled to room temperature, drawn off by suction after one hour, washed with 100 ml petroleum ether and dried.

Yield: 57.3 g E/Z mixture (70/30), 98.2%, M.pt. 122°–8° C. The total yield is 96%.

EXAMPLE 6

If 1.2 g sodium tert-butoxide (2% by weight in relation to residual dimethomorph) is added to the product of Example 5 and a reaction time of 8 hours is used, the yield is 60.7 g E/Z mixture (52/48), 98.8%, M.pt. 125°–143° C.

EXAMPLE 7

Isomerisation can also be carried out using sodium methoxide, used as a 30% methanolic solution.

In this case, the toluene filtrate of Example 5 is dried azeotropically by distilling off 100 ml, the appropriate quantity of sodium methoxide solution is added and the mixture then stirred for 16 hours under reflux. After cooling to 60° C., it is extracted 3 times with 50 ml portions of water and 650 ml is distilled off on a rotary evaporator. After cooling to 50° C., 250 ml petroleum ether is run in under vigorous stirring. The precipitate is left to stand for 1 hour and then drawn off by suction, washed with 100 ml petroleum ether and dried.

When 5% by weight sodium methoxide is used in relation to residual dimethomorph, that is, 10 g 30% solution, the yield is 56.4 g, E/Z mixture (50/50), 98.0%, M.pt. 127°–145°.

When 2% by weight sodium methoxide is used, that is, 4.0 g 30% solution, the yield is 55.7 g, E/Z mixture (52/48), 98.1%, m.pt. 125°–143° C.

We claim:

1. A method of combating fungus on plants which comprises contacting the roots of the plants with an effective fungicidal amount of the Z-isomer of 4-[3-(4-chlorophenyl)-3-(3,4-dimethoxyphenyl)-acryloyl]morpholine.

2. The method of claim 1 wherein the Z-isomer is applied by means of a soil drench.

3. The method of claim 1 wherein the amount of the Z-isomer is in the range of from 0.01 kg/ha to 10.0 kg/ha.

* * * * *